(12) United States Patent
Dieing et al.

(10) Patent No.: US 6,682,725 B1
(45) Date of Patent: Jan. 27, 2004

(54) HIGH MOLECULAR WEIGHT MASS CATIONIC COPOLYMERS

(75) Inventors: Reinhold Dieing, Schifferstadt (DE); Peter Hössel, Schifferstadt (DE); Stephan Kothrade, Limburgerhof (DE); Axel Sanner, Frankenthal (DE); Katrin Zeitz, Ludwigshafen (DE); Hans-Jürgen Raubenheimer, Ketsch (DE); Volker Schehlmann, Römerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/122,097

(22) Filed: Jul. 24, 1998

(51) Int. Cl.[7] ............................. A61K 7/06; A61K 7/11; A61K 7/075; A61K 7/08
(52) U.S. Cl. ................ 424/70.11; 424/70.1; 424/70.15; 424/70.16; 424/70.21; 424/401
(58) Field of Search .............................. 424/70.1, 70.11, 424/70.15, 70.16, 70.21, 401

(56) References Cited

U.S. PATENT DOCUMENTS

| | | | | |
|---|---|---|---|---|
| 4,058,491 A | | 11/1977 | Steckler ...................... 260/2.2 |
| 4,348,380 A | | 9/1982 | Jacquet et al. ................. 424/47 |
| 4,451,582 A | | 5/1984 | Denzinger et al. ............. 521/38 |
| 4,517,175 A | * | 5/1985 | Iwabuchi et al. .............. 424/47 |
| 4,806,345 A | | 2/1989 | Bhattacharyya .............. 424/70 |
| 4,841,066 A | | 6/1989 | Goertz et al. ................ 548/335 |
| 4,859,756 A | | 8/1989 | Goertz et al. ................ 526/263 |
| 5,275,809 A | | 1/1994 | Chen et al. .................... 424/70 |
| 5,804,173 A | * | 9/1998 | Hutchins et al. | |
| 5,869,032 A | * | 2/1999 | Tropsch et al. ............... 424/47 |

FOREIGN PATENT DOCUMENTS

| | | | |
|---|---|---|---|
| EP | 544158 | | 11/1992 |
| EP | 521665 | | 1/1993 |
| EP | 521666 | | 1/1993 |
| EP | 522755 | | 9/1995 |
| EP | 671157 | | 9/1995 |
| EP | 0 715 843 | * | 6/1996 |
| WO | 93/25595 | | 12/1993 |
| WO | 96/26229 | | 8/1996 |
| WO | 96/37525 | | 11/1996 |

* cited by examiner

Primary Examiner—Thurman K. Page
Assistant Examiner—Marina Lamm
(74) Attorney, Agent, or Firm—Keil & Weinkauf

(57) ABSTRACT

The disclosure is directed to a process of conditioning hair in which a cosmetic composition is applied to the hair, which composition contains a polymer formed by (i) the free-radically initiated copolymerization of monomer mixtures of
 (a) from 1 to 99.99% by weight of a cationic monomer or quaternizable monomer,
 (b) from 0 to 98.99% by weight of a water-soluble monomer,
 (c) from 0 to 50% by weight of a further free-radically copolymerizable monomer, and
 (d) from 0.01 to 10% by weight of a bifunctional or polyfunctional, free-radical copolymerizable monomer, and
(ii) subsequent quaternization of the polymer if the monomer (a) is a non-quaternized monomer.

6 Claims, No Drawings

HIGH MOLECULAR WEIGHT MASS CATIONIC COPOLYMERS

The present invention relates to the use of polymers obtainable by free-radically initiated copolymerization of monomer mixtures comprising
  (a) from 1 to 99.99% by weight of a cationic monomer or quaternizable monomer,
  (b) from 0 to 98.99% by weight of a water-soluble monomer,
  (c) from 0 to 50% by weight of a further free-radically copolymerizable monomer, and
  (d) from 0.01 to 10% by weight of a bifunctional or polyfunctional, free-radically copolymerizable monomer,
and subsequent quaternization of the polymer if the monomer (a) employed is a non-quaternized monomer, as active ingredients in cosmetic formulations, preferably in cosmetic hair formulations, especially as conditioning agents in shampoos.

Cationic polymers are employed as conditioning agents in cosmetic formulations. They bring about primarily an improvement in the wet combability of the hair. In addition, cationic polymers prevent electrostatic charging of the hair.

In shampoos, cationic cellulose derivatives (polyquaternium 10) are primarily employed. However, with these compounds a build-up effect is observed; in other words, on repeated use the hair becomes coated with the conditioner and has a heavy feel.

In addition, copolymers of acrylamide and dimethyldiallylammonium chloride (polyquaternium 7) are used. These compounds have the disadvantage, however, of high residual monomer contents, since acrylamide and dimethyldiallylammonium chloride have unfavorable copolymerization parameters.

Quaternized polymers and their use as conditioning agents in haircare formulations are known.

For instance, EP 246 580 describes the use of homo- and copolymers of 3-methyl-1-vinylimidazolium chlorides, inter alia, as hair conditioning agents. EP 544 158 and U.S. Pat. No. 4,859,756 claim the use of homo- and copolymers of chloride-free quaternized N-vinylimidazoles in cosmetic formulations. EP 715 843 discloses the use of copolymers of a quaternized N-vinylimidazole, N-vinylcaprolactam and N-vinylpyrrolidone and, optionally, a further comonomer in cosmetic formulations.

None of said patents describes the use of crosslinked polymers.

DE 3209224 describes the preparation of crosslinked polymers based on N-vinylpyrrolidone and (quaternized) N-vinylimidazole. These polymers are claimed for use as adsorbents and ion exchangers. They are highly crosslinked, insoluble in water and of poor swellability and are therefore unsuitable as conditioning agents in cosmetic formulations.

U.S. Pat. No. 4,058,491 discloses crosslinked cationic hydrogels formed from N-vinylimidazole or N-vinylpyrrolidone and a quaternized basic acrylate along with other comonomers. These gels are proposed for the complexing and controlled release of anionic active substances.

WO 96/26229 describes crosslinked copolymers of N-vinylimidazoles and, inter alia, quaternized N-vinylimidazoles. The polymers are proposed as additives to detergent formulations for inhibiting dye transfer and as adsorbents. They are insoluble in water and unsuitable for cosmetic formulations.

WO 96/37525 describes the preparation of crosslinked copolymers of, inter alia, N-vinylpyrrolidone and quaternized vinylimidazoles in the presence of polymerization regulators, and their use, in particular, in detergents.

DE 4213971 describes copolymers of an unsaturated carboxylic acid, quaternized vinylimidazole and, optionally, further monomers and a crosslinker. The polymers are proposed as thickeners and dispersants.

DE 2821239 (U.S. Pat. No. 4,348,380) describes copolymers of quaternized diallylammonium compounds in cosmetic hair formulations. The polymers are not crosslinked.

DE 3106974 claims a hair treatment composition of the pre-shampoo type, which comprises homo- and copolymers of quaternized diallylammonium compounds. No crosslinker is mentioned.

U.S. Pat. No. 5,275,809, EP 522 755, EP 521 665 and EP 521 666 claim copolymers with dimethyldiallylammonium chloride for use in shampoos. None of these documents describes a crosslinked polymer.

U.S. Pat. No. 4,806,345 cites crosslinked cationic thickeners for cosmetic formulations comprising quaternized dimethylaminoethyl methacrylate and acrylamide.

WO 93/25595 cites crosslinked cationic copolymers based on quaternized dialkylaminoalkyl acrylates or dialkylaminoalkylacrylamides. The proposed use of these crosslinked copolymers is as thickeners in cosmetic formulations, for example in shampoo formulations.

It is an object of the present invention to find a cationic conditioning agent for shampoos which has improved activity and no build-up effect.

We have found that this object is achieved by the crosslinked polymers defined at the outset, which have a very good conditioning action in shampoos, whereas the corresponding non-crosslinked polymers show little activity as conditioning agents in shampoos.

The use in accordance with the invention relates to polymers obtainable by (i) free-radically initiated copolymerization of monomer mixtures comprising
  (a) from 1 to 99.99% by weight, preferably from 2 to 70% by weight and, with particular preference, from 2 to 50% by weight of a cationic monomer or quaternizable monomer,
  (b) from 0 to 98.99% by weight, preferably from 22 to 97.98% by weight and, with particular preference, from 45 to 97.95% by weight of a water-soluble monomer,
  (c) from 0 to 50% by weight, preferably from 0 to 40% by weight and, with particular preference, from 0 to 30% by weight of a further free-radically copolymerizable monomer, and
  (d) from 0.01 to 10% by weight, preferably from 0.02 to 8% by weight and, with particular preference, from 0.05 to 5% by weight of a bi- or polyfunctional, free-radically copolymerizable monomer,
and (ii) subsequent quaternization of the polymer if the monomer (a) employed is a non-quaternized monomer, as conditioning agents for compositions in hair cosmetology.

Suitable monomers (a) are the N-vinylimidazole derivatives of the formula (I), in which $R^1$ to $R^3$ are hydrogen, $C_1$–$C_4$-alkyl or phenyl.

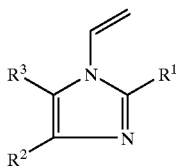

(I)

Also suitable are diallylamines of the formula (II), in which $R^4$ is $C_1$–$C_{24}$-alkyl.

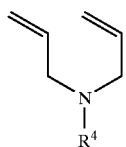

(II)

Additionally suitable are N,N-dialkylaminoalkyl acrylates and methacrylates, and N,N-dialkylaminoalkylacrylamides and -methacrylamides, of the formula (III),

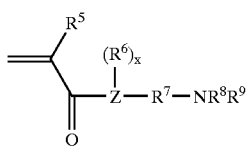

(III)

where $R^5$ and $R^6$ independently are hydrogen or methyl, $R^7$ is optionally alkyl-substituted $C_1$–$C_{24}$-alkylene and $R^8$ and $R^9$ are $C_1$–$C_{24}$-alkyl. Z is nitrogen if x=1 or is oxygen if x=0.

Examples of compounds of the formula (III) are

N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)-butyl]methacrylamide, N-[8-(dimethylamino)octyl]methacrylamide, N-[12-(dimethylamino)dodecyl]methacrylamide, N-[3-(diethylamino)propyl]methacrylamide and N-[3-(diethylamino)propyl]acrylamide.

Examples of compounds suitable for quaternizing the compounds of the formulae (I)–(III) are $C_1$–$C_{24}$-alkyl halides, examples being methyl chloride, methyl bromide, methyl iodide, ethyl chloride, ethyl bromide, propyl chloride, hexyl chloride, dodecyl chloride and lauryl chloride, and benzyl halides, especially benzyl chloride and benzyl bromide. Further suitable quaternizing agents are dialkyl sulfates, especially dimethyl sulfate or diethyl sulfate. The basic monomers of the formulae (I)–(III) can also be quaternized with alkylene oxides, such as ethylene oxide or propylene oxide, in the presence of acids.

Quaternization of the monomer or of a polymer with one of said quaternizing agents can be carried out by conventional methods.

Preferred quaternizing agents are methyl chloride, dimethyl sulfate and diethyl sulfate.

Preferred examples of monomers (a) are 3-methyl-1-vinylimidazolium chloride and methosulfate, dimethyldiallylammonium chloride, and also N,N-dimethylaminoethyl methacrylate and N-[3-(dimethylamino)propyl]methacrylamide which have been quaternized by methyl chloride, dimethyl sulfate or diethyl sulfate.

Particularly preferred monomers (a) are 3-methyl-1-vinylimidazolium chloride and methosulfate and dimethyldiallylammonium chloride, with very particular preference being given to 3-methyl-1-vinylimidazolium chloride and methosulfate.

Suitable water-soluble monomers (b) are N-vinyllactams, examples being N-vinylpiperidone, N-vinylpyrrolidone and N-vinylcaprolactam, N-vinylacetamide, N-methyl-N-vinylacetamide, acrylamide, methacrylamide, N,N-dimethylacrylamide, N-methylolmethacrylamide, N-vinyloxazolidone, N-vinyltriazole, hydroxyalkyl (meth) acrylates, such as hydroxyethyl (meth)acrylate and hydroxypropyl (meth)acrylate, or alkylethylene glycol (meth) acrylates having 1 to 50 ethylene glycol units in the molecule.

Also suitable are N-vinylimidazoles of the formula (I) in which $R^1$ to $R^3$ are hydrogen, $C_1$–$C_4$-alkyl or phenyl, diallylamines of the formula (II), and dialkylaminoalkyl (meth)acrylates and dialkylaminoalkyl(meth)acrylamides of the formula (III), such as dimethylaminoethyl methacrylate or dimethylaminopropylmethacrylamide.

Suitability extends to unsaturated carboxylic acids, examples being acrylic, methacrylic, crotonic, itaconic, maleic and fumaric acid, and their corresponding anhydrides, and also to unsaturated sulfonic acids, such as acrylamidomethylpropanesulfonic acid.

As monomers (b) it is preferred to employ N-vinyllactams. N-Vinylpyrrolidone is very particularly preferred.

Suitable monomers (c) are $C_1$–$C_{24}$-, especially $C_1$–$C_{10}$-alkyl esters of (meth)acrylic acid, for example methyl, ethyl, tert-butyl, isobutyl and n-butyl (meth)acrylates, and acrylamides, such as N-tert-butylacrylamide or N-tert-octylacrylamide. Also suitable are vinyl carboxylates, such as vinyl acetate or vinyl propionate.

Monomers (d), which possess a crosslinking function, are compounds having at least 2 ethylenically unsaturated, nonconjugated double bonds in the molecule.

Suitable crosslinkers are, for example, acrylic esters, methacrylic esters, allyl ethers or vinyl ethers of at least dihydric alcohols. The OH groups of the parent alcohols may be in fully or partially etherified or esterified form; however, the crosslinkers contain at least two ethylenically unsaturated groups.

Examples of the parent alcohols are dihydric alcohols such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis (hydroxymethyl)cyclohexane, neopentyl glycol mono (hydroxypivalate), 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and also polyethylene glycols, polypropylene glycols and polytetrahydrofurans each having molecular weights of from 200 to 10,0090. In addition to the homopolymers of ethylene oxide and/or propylene oxide it is also possible to employ block copolymers of ethylene oxide or propylene oxide or copolymers comprising incorporated ethylene oxide and propylene oxide groups. Examples of parent alcohols having more than two OH groups are trimethylolpropane, glycerol, pentaerythritol, 1,2,5-pentanetriol, 1,2,6-hexanetriol, triethoxycyanuric acid, sorbitan, and sugars such as sucrose, glucose and mannose. The polyhydric alcohols can of course also be employed after reaction with ethylene oxide or propylene oxide, as the corresponding ethoxylates or propoxylates, respectively. The polyhydric alcohols can also first be converted into the corresponding glycidyl ethers by reaction with epichlorohydrin.

Further suitable crosslinkers are the vinyl esters or the esters of monohydric unsaturated alcohols with ethylenically unsaturated $C_3$–$C_6$ carboxylic acids, for example acrylic, methacrylic, itaconic, maleic or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. The monohydric unsaturated alcohols can also, however, be esterified with polybasic carboxylic acids, examples being malonic, tartaric, trimellitic, phthalic, terephthalic, citric or succinic acid.

Other suitable crosslinkers are esters of unsaturated carboxylic acids with the polyhydric alcohols described above, examples being esters of oleic, crotonic, cinnamic or 10-undecenoic acid.

Also suitable as monomers (d) are straight-chain or branched, linear or cyclic, aliphatic or aromatic hydrocarbons which have at least two double bonds which in the case of aliphatic hydrocarbons must not be conjugated: examples are divinylbenzene, divinyltoluene, 1,7-octadiene, 1,9-decadiene, 4-vinyl-1-cyclohexene, trivinylcyclohexane or polybutadienes having molecular weights of from 200 to 20,000.

Yet more suitable crosslinkers are the acrylamides, methacrylamides and N-allylamines based on at least dihydric amines. Examples of such amines are 1,2-diaminomethane, 1,2-diaminoethane, 1,3-diaminopropane, 1,4-diaminobutane, 1,6-diaminohexane, 1,12-dodecanediamine, piperazine, diethylenetriamine and isophoronediamine. Also suitable are the amides of allylamine and unsaturated carboxylic acids such as acrylic, methacrylic, itaconic or maleic acid, or at least dibasic carboxylic acids as have been described above.

Triallylamine and triallylmonoalkylammonium salts, for example triallylmethylammonium chloride or triallylmethylammonium methyl sulfate, are also suitable as crosslinkers.

Further suitable compounds are N-vinyl compounds of urea derivatives, at least difunctional amides, cyanurates or urethanes, for example of urea, ethyleneurea, propyleneurea or tartaramide, such as N,N'-divinylethyleneurea or N,N'-divinylpropyleneurea.

Other suitable crosslinkers are divinyldioxane, tetraallylsilane and tetravinylsilane.

It is preferred to employ those crosslinkers which are soluble in the monomer mixture.

Examples of crosslinkers employed with particular preference are methylenebisacrylamide, triallylamine and triallylalkylammonium salts, divinylimidazole, pentaerythritol triallyl ether, N,N'-divinylethyleneurea, products of the reaction of polyhydric alcohols with acrylic or methacrylic acid, methacrylic esters and acrylic esters of polyalkylene oxides or polyhydric alcohols which have been reacted with ethylene oxide and/or propylene oxide and/or epichlorohydrin.

Especially preferred crosslinkers are methylenebisacrylamide, N,N'-divinylethyleneurea and acrylic esters of glycol, butanediol, trimethylolpropane or glycerol, or acrylic esters of glycol, butanediol, trimethylolpropane or glycerol reacted with ethylene oxide and/or epichlorohydrin.

The monomers (a) to (d) can in each case be employed individually or in a mixture with other monomers from the same group.

The polymers can be prepared by the conventional techniques of free-radically initiated polymerization, for example by solution, emulsion, suspension, precipitation, inverse suspension or inverse emulsion polymerization, without the methods which can be used being restricted to these.

Polymerization usually takes place at from 20° C. to 130° C. and at atmospheric or autogenous pressure.

Initiators which can be employed for the free-radical polymerization are the water-soluble and water-insoluble peroxo and/or azo compounds customary for this purpose, examples being alkali metal or ammonium peroxodisulfates, dibenzoyl peroxide, tert-butyl perpivalate, tert-butyl per-2-ethylhexanoate, di-tert-butyl peroxide, tert-butyl hydroperoxide, azobisisobutyronitrile, azobis(2-amidinopropane) dihydrochloride or 2,2'-azobis(2-methylbutyronitrile). Also suitable are initiator mixtures or redox initiator systems, such as ascorbic acid/iron(II) sulfate/sodium peroxodisulfate, tert-butyl hydroperoxide/sodium disulfite, tert-butyl hydroperoxide/sodium hydroxymethanesulfinate. The initiators can be employed in the customary amounts, for example from 0.05 to 5% by weight based on the amount of monomers to be polymerized.

The molecular weight and the K value of the polymers can be varied widely in a manner known per se through the choice of polymerization conditions, such as duration, temperature and initiator concentration, and by the content of crosslinker. The K values of the polymers are within a range from 30 to 350, preferably from 50 to 350.

The K values are measured by the method of Fikentscher, Cellulosechemie 13 (1932) 58–64 at 25° C. on 0.1% strength solutions in 0.5 molar sodium chloride solution.

The novel polymers suitable as conditioning agents in cosmetic formulations, especially cosmetic hair formulations such as hair treatments, hair lotions, hair rinses, hair emulsions, treatment fluids for damaged ends, equalizing agents for permanent waves, hot-oil treatment preparations, conditioners, setting lotions or hair sprays.

Depending on the field of use, the cosmetic hair formulations can be applied in spray, foam, gel, gel spray or mousse form.

In addition to the novel polymers and appropriate solvents, such as water or water/alcohol mixtures, the cosmetic hair formulations may also include customary cosmetics additives, such as emulsifiers, preservatives, perfume oils, care substances such as panthenol, collagen, vitamins, protein hydrolysates, stabilizers, pH regulators, colorants, salts, consistency additives, silicones, humectants, refatting agents and other customary additives.

The novel polymers can also be blended with conventional hair cosmetics polymers if specific properties are to be imparted.

Examples of suitable customary hair cosmetics polymers are anionic polymers. Such anionic polymers are homo- and copolymers of acrylic and methacrylic acid or their salts, copolymers of acrylic acid and acrylamide and salts thereof, sodium salts of polyhydroxycarboxylic acids, water-soluble or water-dispersible polyesters, polyurethanes and polyureas. Particularly suitable polymers are copolymers of t-butyl acrylate, ethyl acrylate and methacrylic acid (eg. Luvimer® 100P), copolymers of ethyl acrylate and methacrylic acid (eg. Luvimer® MAE), copolymers of N-tert-butyl acrylamide, ethyl acrylate and acrylic acid (Ultrahold® 8, strong), copolymers of vinyl acetate, crotonic acid and vinyl propionate (eg. Luviset® CAP), maleic anhydride copolymers, unmodified or reacted with alcohols, anionic polysiloxanes, such as carboxyfunctional polysiloxanes, and copolymers of vinylpyrrolidone, t-butyl acrylate and methacrylic acid (eg. Luviskol® VBM).

Especially preferred anionic polymers are acrylates having an acid number of greater than or equal to 120, and copolymers of t-butyl acrylate, ethyl acrylate and methacrylic acid.

Further suitable hair cosmetics polymers are cationic polymers bearing the INCI designation polyquaternium, such as copolymers of vinylpyrrolidone/N-vinylimidazolium salts (Luviquat® FC, Luviquat® HM, Luviquat® MS), copolymers of N-vinylpyrrolidone/dimethylaminoethyl methacrylate quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium 4 and 10) and acrylamide copolymers (polyquaternium 7).

Neutral polymers are also suitable as further hair cosmetics polymers, such as polyvinylpyrrolidones, copolymers of N-vinylpyrrolidone and vinyl acetate and/or vinyl propionate, polysiloxanes, polyvinylcaprolactam and N-vinylpyrrolidone copolymers, polyethyleneimines and their salts, polyvinylamines and their salts, cellulose derivatives and salts of polyaspartic acid and derivatives.

In order to impart particular properties the formulations may also comprise conditioning substances based on silicone compounds. Examples of suitable silicone compounds are polyalkylsiloxanes, polyarylsiloxanes, polyarylalkylsiloxanes, polyethersiloxanes and silicone resins.

The novel polymers are particularly suitable for use as conditioning agents in shampoo formulations.

The shampoo formulations normally comprise anionic surfactants as base surfactants and amphoteric and nonionic surfactants as cosurfactants.

The formulations contain 2–50% by weight of surfactants, preferably 5–40% by weight and, with particular preference, from 8–30% by weight.

In the shampoo formulations it is possible to use all anionic, neutral, amphoteric or cationic surfactants which are normally employed in shampoos.

Examples of suitable anionic surfactants are alkyl sulfates, alkyl ether sulfates, alkylsulfonates, alkylarylsulfonates, alkylsuccinates, alkylsulfosuccinates, N-alkylsarcosinates, acyltaurates, acylisethionates, alkyl phosphates, alkyl ether phosphates, alkyl ether carboxylates, alpha-olefinsulfonates, especially the alkali metal salts and alkaline earth metal salts, examples being sodium, potassium, magnesium, calcium and also ammonium salts and triethanolamine salts. The alkyl ether sulfates, alkyl ether phosphates and alkyl ether carboxylates can have from 1 to 10 ethylene oxide or propylene oxide units, preferably 1 to 3 ethylene oxide units, in the molecule.

Suitable examples are sodium lauryl sulfate, ammonium lauryl sulfate, sodium lauryl ether sulfate, ammonium lauryl ether sulfate, sodium lauroylsarcosinate, sodium oleylsuccinate, ammonium laurylsulfosuccinate, sodium dodecylbenzenesulfonate and triethanolamine dodecylbenzenesulfonate.

Examples of suitable amphoteric surfactants are alkyl betaines, alkylamidopropyl betaines, alkyl sulfobetaines, alkylglycinates, alkylcarboxyglycinates, alkylamphoacetates or -propionates, alkylamphodiacetates or -dipropionates.

It is possible, for example, to employ cocodimethylsulfopropyl betaine, lauryl betaine, cocamidopropyl betaine or sodium cocamphopropionate.

Nonionic surfactants which are suitable are, for example, the products of reaction of aliphatic alcohols or alkylphenols having 6–20 carbons in the alkyl chain, which can be linear or branched, with ethylene oxide and/or propylene oxide. The amount of alkylene oxide is about 6–60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The shampoo formulations may also include customary cationic surfactants, such as quaternary ammonium compounds, an example of which is cetyltrimethylammonium chloride.

The novel polymers are usually employed at from 0.01 to 5% by weight, preferably from 0.05 to 2% by weight.

It is also possible, in addition, to employ further cationic polymers customary in shampoos, such as copolymers of acrylamide and dimethyldiallylammonium chloride (polyquaternium 7), cationic cellulose derivatives (polyquaternium 10), guar hydroxypropyltrimethylammonium chloride (INCI name: hydroxypropyl guar hydroxypropyltrimonium chloride), copolymers of N-vinylpyrrolidone and quaternized N-vinylimidazole (polyquaternium 16, 44 and 46) et cetera.

The shampoo formulations may also comprise thickeners, such as sodium chloride, PEG-55, propylene glycol oleate, PEG-120 methyl glucose dioleate and others, and also preservatives, further active substances and auxiliaries, and water.

A PREPARING THE POLYMERS

EXAMPLE 1

A stirred apparatus was charged with 400 g of water and 46 g of dimethyldiallylammonium chloride solution (65% strength). To this initial charge there was added 10% of feed stream 1 consisting of 270 g of N-vinylpyrrolidone and 0.6 g of N,N'-divinylethyleneurea. The mixture was heated to 60° C. under nitrogen and with stirring, and the remainder of feed stream 1 was metered in over 3 hours and feed stream 2, consisting of 0.9 g of 2,2'-azobis(2-amidinopropane) dihydrochloride in 100 g of water, was metered in over the course of 4 hours. After 3 hours the reaction mixture was diluted with 700 g of water and stirred for one hour more. Then 1.5 g of 2,2'-azobis(2-amidinopropane) dihydrochloride in 30 g of water were added and stirring was continued at 60° C. for 2 hours more.

This gave a colorless highly viscous polymer solution having a solids content of 20.9% and a K value of 80.3.

EXAMPLE 2

A stirred apparatus was charged with 300 g of feed stream 1, consisting of 200 g of N-vinylpyrrolidone, 77 g of dimethyldiallylammonium chloride solution (65% strength), 1.13 g of N,N'-divinylethyleneurea and 440 g of water and this initial charge was heated to 60° C. under nitrogen and with stirring. The remainder of feed stream 1 was metered in over the course of 2 hours and feed stream 2, consisting of 0.75 g of 2,2'-azobis(2-amidinopropane) dihydrochloride in 100 g of water, was metered in over the course of 4 hours. After the end of feed stream 1 the reaction mixture was diluted with 1620 g of water. After the end of feed stream 2, stirring was continued for one hour more at 60° C. Then 1.25 g of 2,2'-azobis(2-amidinopropane) dihydrochloride in 65 g of water were added and stirring was continued for one hour more. This gave a colorless highly viscous polymer solution having a solids content of 10.2% and a K value of 80.

EXAMPLE 3

A stirred apparatus was charged with 130 g of water and 48 g of 3-methyl-1-vinylimidazolium chloride and this initial charge was heated with stirring and under nitrogen to 60° C. Then feed stream 1, consisting of 192 g of N-vinylpyrrolidone, 0.48 g of N,N'-divinylethyleneurea and 450 g of water, was metered in over the course of 3 hours and feed stream 2, consisting of 1.44 g of 2,2'-azobis(2-amidinopropane) dihydrochloride in 80 g of water, was metered in over the course of 4 hours. Stirring was subsequently continued at 60° C. for one hour. In order to keep the batch stirrable, dilution was carried out as required with a total of 2100 g of water. This gave a colorless, highly viscous polymer solution having a solids content of 8.2% and a K value of 105.

EXAMPLE 4

A stirred apparatus was charged with 716 g of water and this initial charge was heated with stirring and under nitrogen to 60° C. Then feed stream 1, consisting of 180 g of N-vinylpyrrolidone, 20 g of 3-methyl-1-vinylimidazolium methyl sulfate, 0.32 g of N,N'-divinylethyleneurea and 25 g of water, was metered in over the course of 2 hours and feed stream 2, consisting of 0.6 g of 2,2'-azobis(2-amidinopropane)dihydrochloride in 60 g of water, was metered in over the course of 3 hours. After the end of feed stream 1, the reaction mixture was diluted with 1000 g of water. Following feed stream 2, stirring was continued at 70° C. for 3 hours. This gave a colorless, highly viscous polymer solution having a solids content of 11.0% and a K value of 86.

EXAMPLE 5

A stirred apparatus was charged with 440 g of water and this initial charge was heated with stirring and under nitrogen to 60° C. Then feed stream 1, consisting of 180 g of N-vinylpyrrolidone, 20 g of 3-methyl-1-vinylimidazolium methyl sulfate, 0.30 g of N,N'-divinylethyleneurea and 25 g of water, was metered in over the course of 2 hours and feed stream 2, consisting of 0.6 g of 2,2'-azobis(2-amidinopropane)dihydrochloride in 60 g of water, was metered in over the course of 3 hours. Following feed stream 2, stirring was continued at 70° C. for 3 hours. In order to keep the reaction mixture stirrable, dilution was carried out as required with a total of 1275 g of water. This gave a colorless, highly viscous polymer solution having a solids content of 11.3% and a K value of 105.

EXAMPLE 6

A stirred apparatus was charged with 650 g of water and this initial charge was heated with stirring and under nitrogen to 60° C. Then feed stream 1, consisting of 225 g of N-vinylpyrrolidone, 25 g of 2,3-dimethyl-1-vinylimidazolium methyl sulfate, 0.25 g of N,N'-divinylethyleneurea and 580 g of water, was metered in over the course of 3 hours and feed stream 2, consisting of 0.7 g of 2,2'-azobis(2-amidinopropane)dihydrochloride in 100 g of water, was metered in over the course of 4 hours. After the end of feed stream 1, the reaction mixture was diluted with 835 g of water. Following feed stream 2, stirring was continued for one hour more and a further 1.25 g of 2,2'-azobis(2-amidinopropane)dihydrochloride in 77 g of water were added. Then stirring was continued for 2 hours at 70° C. This gave a colorless, highly viscous polymer solution having a solids content of 10.4% and a K value of 106.

EXAMPLE 7

A stirred apparatus was charged with 650 g of water and this initial charge was heated with stirring and under nitrogen to 60° C. Then feed stream 1, consisting of 225 g of N-vinylpyrrolidone, 25 g of 2,3-dimethyl-1-vinylimidazolium methyl sulfate, 0.375 g of N,N'-divinylethyleneurea and 580 g of water, was metered in over the course of 3 hours and feed stream 2, consisting of 0.7 g of 2,2'-azobis(2-amidinopropane)dihydrochloride in 100 g of water, was metered in over the course of 4 hours. After the end-of feed stream 1, the reaction mixture was diluted with 1135 g of water. Following feed stream 2, stirring was continued for one hour more and a further 1.25 g of 2,2'-azobis(2-amidinopropane) dihydrochloride in 77 g of water were added. Then stirring was continued for 2 hours at 70° C. This gave a colorless, highly viscous polymer solution having a solids content of 9.2% and a K value of 92.

EXAMPLE 8

A reaction vessel with nitrogen blanketing was charged with 800 g of cyclohexane, 5 g of sorbitan monooleate, 5 g of Hypermer B246[1] and 1 g of 2,2'-azobis(2,4-dimethylvaleronitrile) and this initial charge was heated to 65° C. The feed stream, consisting of 100 g of 3-methyl-1-vinylimidazolium methyl sulfate, 100 g of N-vinylpyrrolidone, 100 g of water and 0.25 g of tripropylene glycol diacrylate, was metered in over the course of 20 minutes. Then the mixture was stirred at 65° C. for 6 hours. Subsequently, 200 g of cyclohexane were added and the water was distilled off azeotropically, and the polymer was filtered off and dried. The K value of an aqueous solution of the polymer was 114.

[1] Hypermer B24® polymeric surfactant from ICI

EXAMPLE 9

A stirred apparatus was charged with 900 g of ethyl acetate and this initial charge was heated under nitrogen and with stirring to 77° C. Then feed stream 1, consisting of 270 g of N-vinylpyrrolidone, 30 g of I-vinylimidazole and 0.3 g of N,N'-divinylethyleneurea, was metered in over the course of 3 hours and feed stream 2, consisting of 3 g of 2,2'-azobis (2-methylbutyronitrile) in 80 g of ethyl acetate, was metered in over the course of 4 hours. The mixture was then stirred for 2 hours and cooled to room temperature, and 36 g of dimethyl sulfate were added. It was subsequently stirred for half an hour at room temperature and for 2 hours more at 70° C. The resulting powder was filtered off and dried. The K value of an aqueous solution of the polymer was 125.

EXAMPLE 10

A stirred apparatus was charged with 440 g of water and this initial charge was heated under nitrogen and with stirring to 60° C. Then feed stream 1, consisting of 144 g of N-vinyl-pyrrolidone, 16 g of 3-methyl-1-vinylimidazolium methylsulfate, 1.4 g of tetraethylene glycol diacrylate and 100 g of water, was metered in over the course of 2 hours and feed stream 2, consisting of 0.8 g of 2,2'-azobis(2-amidinopropane)dihydrochloride in 50 g of water, was metered in over the course of 3 hours. Following feed stream 2, the mixture was stirred for 3 hours at 70° C. In order to keep the reaction mixture stirrable, it was diluted as required with a total of 1200 g of water. This gave a colorless, highly viscous polymer solution having a solids content of 8.5% and a K value of 95.

EXAMPLE 11

A stirred apparatus was charged with 550 g of water and this initial charge was heated under nitrogen and with stirring to 60° C. Then feed stream 1, consisting of 102 g of N-vinyl-pyrrolidone, 26 g of 3-methyl-1-vinylimidazolium methylsulfate, 0.8 g of triallylamine and 100 g of water, was metered in over the course of 2 hours and feed stream 2, consisting of 0.6 g of 2,21-azobis(2-amidinopropane) dihydrochloride in 50 g of water, was added to the reaction mixture over 3 hours. Following feed stream 2, the mixture was stirred for 3 hours at 70° C. In order to keep the reaction mixture stirrable, it was diluted as required with a total of 1000 g of water. This gave a pale yellowish, highly viscous polymer solution having a solids content of 7.0% and a K value of 102.

EXAMPLE 12

Example 11 was repeated but replacing the triallylamine by 2.2 g of pentaerythritol triallyl ether. This gave a pale yellowish, highly viscous polymer solution having a K value of 95.

EXAMPLE 13

A stirred apparatus was charged with 440 g of water and this initial charge was heated under nitrogen and with stirring to 60° C. Then feed stream 1, consisting of 150 g of N-vinyl-pyrrolidone, 8 g of 3-methyl-1-vinylimidazolium methylsulfate, 0.6 g of triallylamine and 100 g of water, was metered in over the course of 2 hours and feed stream 2, consisting of 0.8 g of 2,2'-azobis(2-amidinopropane) dihydrochloride in 50 g of water, was metered in over the course of 3 hours. Following feed stream 2, the mixture was stirred for 3 hours at 70° C. In order to keep the reaction mixture stirrable, it was diluted as required with a total of 1200 g of water. This gave a colorless, highly viscous polymer solution having a solids content of 8.1% and a K value of 98.

EXAMPLE 14

A reaction vessel with nitrogen flushing was charged with 800 g of cyclohexane, 5 g of sorbitan monooleate and 5 g of Hypermer B246[2] and this initial charge was heated to 60° C. Feed stream 1, consisting of 60 g of 3-methyl-1-vinylimidazolium methylsulfate, 140 g of N-vinylpyrrolidone, 150 g of water and 1.0 g of triallylamine, and feed stream 2, consisting of 0.6 g of 2,21'-azobis(2-amidinopropane) dihydrochloride in 50 g of water, were metered in over the course of 1 hour. The mixture was subsequently stirred at 60° C. for a further 6 hours. Then 200 g of cyclohexane were added and the water was distilled off azeotropically; the polymer was isolated by filtration and dried.

2 Hypermer B24® polymeric surfactant from ICI

EXAMPLE 15

A reaction vessel with nitrogen flushing was charged with 800 g of cyclohexane, 5 g of sorbitan monooleate and 5 g of Hypermer B246[3] and this initial charge was heated to 60° C. Feed stream 1, consisting of 20 g of 3-methyl-1-vinylimidazolium methylsulfate, 180 g of N-vinylpyrrolidone, 150 g of water and 0.5 g of triallylamine, was metered in over the course of 1 hour and feed stream 2, consisting of 1.2 g of 2,2'-azobis(2-amidinopropane)dihydrochloride in 70 g of water, was metered in over the course of 4 hours. The mixture was subsequently stirred at 60° C. for a further 3 hours. Then 200 g of cyclohexane were added and the water was distilled off azeotropically; the polymer was isolated by filtration and dried.

3 Hypermer B24® polymeric surfactant from ICI

EXAMPLE 16

A stirred apparatus was charged with 400 g of water, 100 g of N-vinylpyrrolidone, 11 g of 3-methyl-1-vinylimidazolium methylsulfate and 0.4 g of triallylamine and this initial charge was heated under nitrogen and with stirring to 60° C. Then feed stream 1, consisting of 0.6 g of 2,2'-azobis(2-amidinopropane)dihydrochloride in 50 g of water, was added to the reaction mixture over 3 hours, and the resulting mixture was diluted with 1000 g of water. This mixture was subsequently stirred at 80° C. for 3 hours. This gave a colorless, highly viscous polymer solution having a solids content of 7.6% and a K value of 110.

B USING THE POLYMERS AS CONDITIONING AGENTS

EXAMPLEs 17–21

In the following examples 6 shampoos were prepared according to the formulation below, using the polymers from EXAMPLEs 1–15, and their properties as hair cosmetics were determined.

EXAMPLEs 22–24

Comparative Experiments 3 shampoos were prepared according to the formulation below but using cationic polymers which contained no crosslinker.

Shampoo formulation for examples 16–24 in Table 1:

| | |
|---|---|
| Sodium lauryl ether sulfate | 10.0% |
| Cocamidopropyl betaine | 4.0% |
| Polymer (from Examples 1–15) | 0.1 or 0.5% |
| Water | to 100% |

Test Methods a) Wet/dry Combability

A tensile/pressure testing machine is used to determine the combing force required to draw a comb through a tress of hair. The decrease in combing force is calculated as follows (the larger the figure the better the shampoo).

% decrease in combing force=100 (1 −Ay/Ao)

Ay=Combing force after treatment with test shampoo (see examples)

Ao=Combing force after treatment with shampoo without polymer (control)

b) Foam Creaminess

Subjective evaluation using a rating scale from 1 (very good) to 3 (weak)

Both the combability of the hair and the foam creaminess are influenced by the nature and amount of polymer.

TABLE 1

Performance tests with the above mentioned test shampoo

| Shampoo Example No. | Preparation Example No. | Decrease in combing force, wet 0.1%/0.5% polymer | Decrease in combing force, dry 0.5% polymer | Foam creaminess (Rating) |
|---|---|---|---|---|
| 17 | 1 | 47%/57% | — | Very good |
| 18 | 4 | 55%/64% | 48% | Very good |
| 19 | 7 | 52%/60% | — | Very good |
| 20 | 11 | 37%/55% | — | Very good |
| 21 | 14 | 62%/65% | — | Very good |
| 22 | 15 | 51%/66% | — | Very good |
| 23 | Polyquaternium 16 | 0%/19% | minus 40% | Weak |
| 24 | Polyquaternium 7 | 12%/24% | 24% | Good |
| 25 | Polyquaternium 10 | | | |

Examples 17–22 clearly show the outstanding properties in the case of use in accordance with the invention, as compared with conventional use (Examples 23–25).

We claim:

1. A process of conditioning hair comprising applying to the hair a cosmetic hair composition comprising a polymer obtained by (i) free-radically initiated copolymerization of monomer mixtures comprising (a) from 1 to 99.99% by weight of a cationic monomer or quaternizable monomer, (b) from 0 to 98.99% by weight of a water-soluble monomer, (c) from 0 to 50% by weight of a further free-radically copolymerizable monomer, and (d) from 0.01 to 10% by weight of a bifunctional or polyfunctional, free-radically copolymerizable monomer, and (ii) subsequent quaternization of the polymer if the monomer (a) is a non-quaternized monomer, wherein the monomer (a) is an N-vinylimidazole derivative of the formula (I)

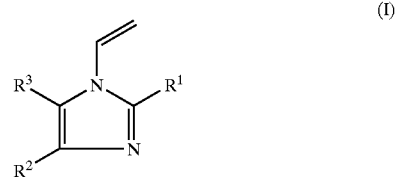

where $R^1$ to $R^3$ are hydrogen, $C_1$–$C_4$-alkyl or phenyl, wherein said N-vinylimidazole derivative of the formula (I) may optionally be in a quaternized form, wherein the monomer (b) is N-vinyl-pyrrolidone,
   wherein said polymer acts on the hair as conditioning agent and
   wherein the cosmetic hair composition further comprises from 2 to 50% by weight of surfactants.

2. The process of claim 1 where the monomer (c) is a $C_1$–$C_{24}$-alkyl ester of (meth)acrylic acid.

3. The process of claim 1, wherein the cosmetic hair composition comprises 0.05 to 2% by weight of the polymer.

4. The process of claims 1, wherein the cosmetic hair composition further comprises from 8 to 30% by weight of surfactants.

5. The process of claim 1, wherein the cosmetic hair composition further comprises shampoo.

6. The process of claim 1, herein the monomer (c) is a $C_1$–$C_{24}$-alkyl ester of (meth)acrylic acid and the cosmetic hair composition further comprises 0.05 to 2% by weight of the polymer.

* * * * *

UNITED STATES PATENT AND TRADEMARK OFFICE
CERTIFICATE OF CORRECTION

PATENT NO. : 6,682,725 B1
DATED : January 27, 2004
INVENTOR(S) : Dieing et al.

It is certified that error appears in the above-identified patent and that said Letters Patent is hereby corrected as shown below:

<u>Title page,</u>
Item [54], Title, delete "WEIGHT".
Insert the following:
-- [30] Foreign Application Priortiy Data
  Jul. 24, 1997 (DE) ...................... 197 31 764 --.

<u>Column 14,</u>
Line 30, "claims" should be -- claim --;
Line 35, "herein" should be -- wherein --.

Signed and Sealed this

Sixth Day of July, 2004

JON W. DUDAS
*Acting Director of the United States Patent and Trademark Office*